(12) United States Patent
Vadivelu (10) Patent No.: US 11,839,718 B2
(45) Date of Patent: Dec. 12, 2023

(54) ORAL GAS CATHETER AND METHOD OF INDUCING GAS IN A PATIENT

(71) Applicant: Shanmugham Vadivelu, Chesterton, IN (US)

(72) Inventor: Shanmugham Vadivelu, Chesterton, IN (US)

(*) Notice: Subject to any disclaimer, the term of this patent is extended or adjusted under 35 U.S.C. 154(b) by 0 days.

(21) Appl. No.: 17/933,217

(22) Filed: Sep. 19, 2022

(65) Prior Publication Data
US 2023/0102953 A1 Mar. 30, 2023

Related U.S. Application Data

(60) Provisional application No. 63/360,369, filed on Sep. 28, 2021.

(51) Int. Cl.
*A61M 16/04* (2006.01)
*A61B 5/083* (2006.01)

(52) U.S. Cl.
CPC ....... *A61M 16/0493* (2014.02); *A61B 5/0836* (2013.01); *A61M 2202/0208* (2013.01)

(58) Field of Classification Search
CPC ...... A61M 16/0493; A61M 2205/0625; A61M 16/0666; A61M 16/0672; A61M 16/085; A61M 16/0463; A61M 16/049; A61B 5/097
See application file for complete search history.

(56) References Cited

U.S. PATENT DOCUMENTS

| | | | |
|---|---|---|---|
| 9,414,899 B2* | 8/2016 | Altounian | A61J 7/0015 |
| 2005/0103331 A1* | 5/2005 | Wedemeyer | A61B 90/02 128/207.14 |
| 2008/0027344 A1* | 1/2008 | Terry | A61M 16/0666 600/532 |
| 2010/0016908 A1* | 1/2010 | Martin | A61M 16/049 607/3 |
| 2010/0016909 A1* | 1/2010 | Gachiengo | A61N 1/3752 607/4 |
| 2020/0188622 A1* | 6/2020 | Borvan | A61M 16/0495 |

* cited by examiner

*Primary Examiner* — Margaret M Luarca
(74) *Attorney, Agent, or Firm* — Hartman Global IP Law; Gary M. Hartman; Domenica N. S. Hartman (57) ABSTRACT

Oral gas catheters and methods of inducing gas in a patient orally. The oral gas catheter includes one or more delivery cannulas configured to be inserted into the patient's mouth with a distal end of the delivery cannula disposed adjacent the patient's laryngeal inlet, and a clip disposed on the delivery cannula. The clip is configured to secure the delivery cannula to a tooth of the patient. The oral gas catheter may have two such delivery cannulas and clips with the delivery cannulas coupled together by a coupler. The delivery cannulas are placed in an operative position in a patient's mouth and secured in the operative position by releasably securing the clips to the patient's teeth. The oral gas catheter makes it possible to bypass the nasal cavity and deliver oxygen or other gas directly adjacent the laryngeal entrance and into an anatomical dead space of the airway.

18 Claims, 5 Drawing Sheets

ORAL GAS CATHETER AND METHOD OF INDUCING GAS IN A PATIENT

CROSS-REFERENCE TO RELATED APPLICATIONS

This application claims the benefit of U.S. Provisional Application No. 63/360,369, filed Sep. 28, 2021, the contents of which are incorporated herein by reference.

BACKGROUND OF THE INVENTION

The invention relates generally to oral gas catheters and methods of inducing gas in a patient.

An oxygen catheter is a flexible tubular medical device used in clinical and surgery settings for inducing oxygen into the lungs so that the oxygen level in blood is maintained at desired levels. An oxygen catheter is more significant in oxygen application when a patient experiences hypoxic states during emergency surgeries or while being monitored in an intensive care unit (ICU). Typically, the oxygen catheter's sole purpose is to supply oxygen continuously so that patients do not succumb to hypoxic states that can range from mild to severe.

Figure 1:
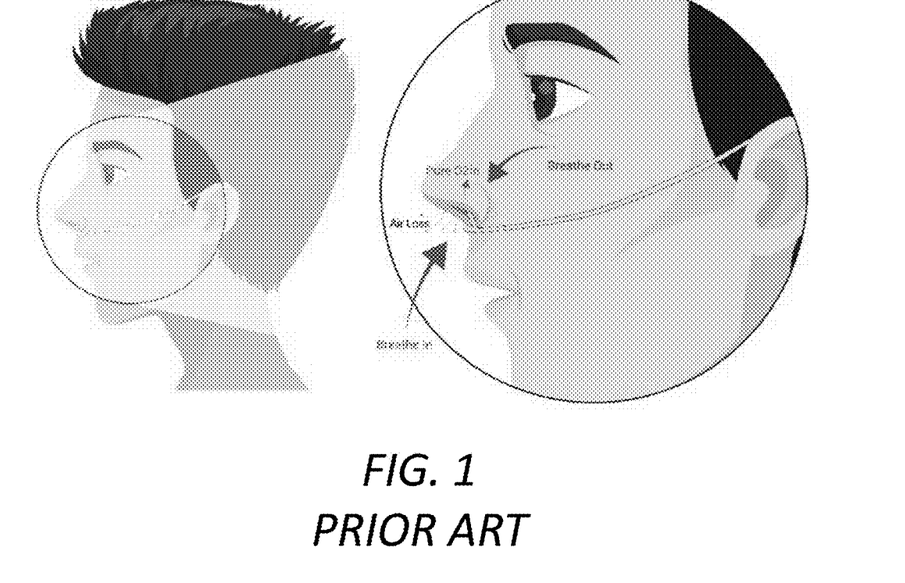
FIG. 1 illustrates operative placement of a typical nasal oxygen catheter on a patient.

There are several types of oxygen catheters used in respiratory care, including catheters connected with nasal masks, catheters connected with nebulizer masks, catheters connected with venturi masks, and catheters connected with nasal cannula. The last of these types of oxygen catheters are called nasal application catheters (also nasal oxygen catheters or nasal catheters) in that each of these oxygen catheters is applied externally through a nasal passage. As illustrated in FIG. 1, in use, the distal end of a nasal oxygen catheter from which oxygen flows is placed externally at the nostril entrance.

In the area of patient anesthetization, there are two broad categories of anesthesia applications: general and regional anesthesia applications, and monitored anesthesia care (MAC)-assisted operative procedures. In monitored anesthesia care, a patient is sedated in one of three possible states depending on the complexity of the procedure: a mild, moderate, or deep state of sedation. It is estimated that about fifty to sixty percent of anesthetic procedures are done under MAC, most of which come under outpatient services. A non-exhaustive list of procedures aided by MAC includes endoscopy, minor orthopedic procedures, eye surgery, podiatric procedures, dental procedures, minor surgical procedures, minor cardiology procedures, radiology procedures, gynecology procedures, biopsy, and bronchoscopy.

Although there are many benefits of MAC-assisted operative procedures, such procedures also pose implementation challenges to anesthetists because patients are typically in dynamically varying sedative states during MAC-assisted operative procedures. For example, it can be challenging to effectively monitor oxygenation of a patient's sedative state, to supply effective oxygenation, and/or to rescue and secure the airway in the event of an anesthetic procedural complication. A common thread that encompasses all these challenges deals with timely administration of oxygen across the dynamically varying sedative states. Other common challenges can include partial airway obstruction, tongue fallback, and breathing failure. In addition, complex surgeries often require that anesthetic catheters share mouth and throat spaces with other surgical catheters and endoscopes, which raises the risk of losing airway and oxygenation of the patient.

Typically, oxygen during MAC-assisted operative procedures is supplied with some type of nasal oxygen catheter. Some of the challenges encountered during MAC-assisted operative procedures identified above, as well as other challenges, can be caused or exacerbated by the external placement of a nasal oxygen catheter at the nostril entrance. For example, because of the placement of the nasal catheter at nose level that is farthest from lungs entry point, it can be very difficult to efficiently oxygenate patients through nasal catheters if complications, such as varying anesthetic depth, arise during an operative procedure under MAC. In hypoxic situations, it may not be possible to efficiently augment oxygen tension and nasopharyngeal pressure due to the external catheter placement. Some additional challenges that can arise due to the external placement of a nasal oxygen catheters include, for example, the following. Increasing blood oxygen level takes a longer time, which requires higher inflow of oxygen to thrust into the lungs, resulting in oxygen loss into the atmosphere, and typically attains 80% oxygen saturation only after about four to five minutes of inflow. Despite the administration of high inflow of oxygen, anatomical dead space in the airway on the order of about 120 to 150 ml is not fully charged. As known in the art and schematically represented in FIG. 2, an anatomical dead space is a natural fixed space within an airway that is bound by surrounding structures and in which gases (e.g., air, oxygen, anesthesia, etc.) are able to move in and out of, but a volume of the gas within the dead space does not participate in gas exchange in the lung. Without added humidification, the higher flow oxygen application can cause nasal dryness, which in turn can cause irritation in the nasal pathway or even cause toxic nasal inflammation in some patients. When there is nasal bleeding or block, it is extremely difficult to administer a nasal catheter and effectively adjust the oxygen flow rate. In longer duration applications where nasal masks are used, the nasal mask can be uncomfortable to the patient and are harder for the patient to tolerate, especially when being treated for trauma and/or bleeding. If a procedure requires monitoring of the volume of carbon dioxide ($CO_2$) exhaled by the patient, an additional catheter to record $CO_2$ is typically required in tandem with the nasal oxygen catheter.

Figure 2:
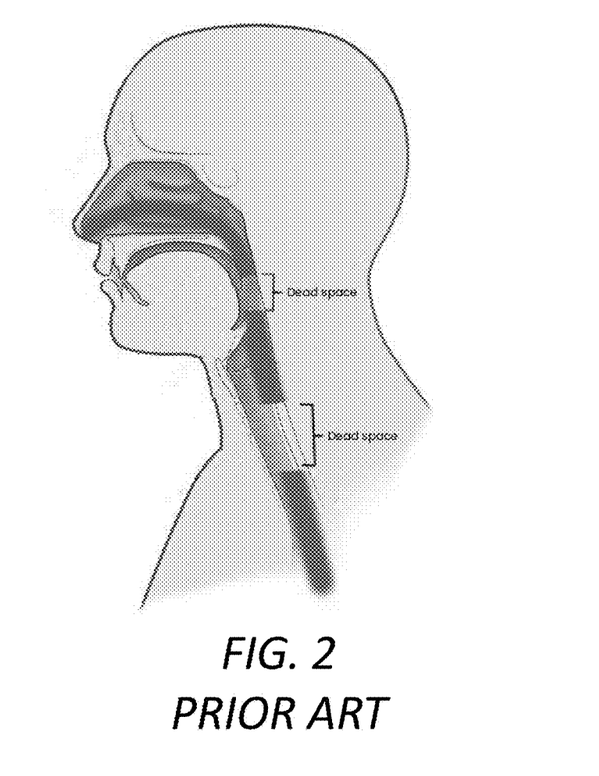
FIG. 2 illustrates the air flow path of oxygen from the nasal oxygen catheter from the nostril to the trachea.

As can be seen in FIG. 2, the nasal air pathway (from the nostril to the lungs) is longer than the oral pathway (from the mouth to the lungs). The oxygen saturation efficiency applied on patients is limited owing to the longer nasal pathway. In addition, the exchange of gases, typically oxygen and carbon dioxide, create intermittent anatomical dead spaces in the air pathway, as shown in FIG. 2. From an anesthetist's perspective, the presence of dead spaces in the air pathway is a significant problem that needs to be addressed during deep sedation for some surgical procedures. Typically, this requires application of a higher flow of oxygen through a nasal catheter, where the anesthetist calibrates the intensity of oxygen flow manually, so that rhythmic breathing is established. In obese patients, dead space in the lungs is more complex to calibrate, and anesthetists and nurses work in tandem to calibrating oxygen flow manually while adjusting the patient's head and neck accordingly.

It would be desirable to have an oxygen catheter for use, for example during MAC-assisted operative procedures, which overcomes or reduces one or more of the challenges discussed above.

BRIEF SUMMARY OF THE INVENTION

In one nonlimiting aspect of the invention, an oral gas catheter is provided for administering a gas, such as oxygen or other gas, under pressure into the lungs of a patient. The oral gas catheter includes a delivery cannula configured to be inserted into the patient's mouth with a distal end of the delivery cannula disposed adjacent the patient's laryngeal inlet, and a clip disposed on the delivery cannula. The clip is configured to secure the delivery cannula to a tooth of the patient.

In another nonlimiting aspect of the invention, an oral gas catheter for administering a gas under pressure into the lungs of a patient is provided. The oral gas catheter includes a first delivery cannula configured to be inserted into the patient's mouth with a distal end of the first delivery cannula disposed adjacent the patient's laryngeal inlet, and a second delivery cannula configured to be inserted into the patient's mouth with a distal end of the second delivery cannula disposed adjacent the patient's laryngeal inlet. A first clip is disposed on the first delivery cannula. The first clip is configured to secure the first delivery cannula to a first tooth on one side of the patient's mouth. A second clip is disposed on the second delivery cannula. The second clip is configured to secure the second delivery cannula to a second tooth on a second side of the patient's mouth opposite the first side. A first coupler couples the first delivery cannula to the second delivery cannula. The first and second clips are disposed between the first coupler and the respective distal ends of the first and second cannulas.

In still another nonlimiting aspect of the invention, a method of inducing a gas in a patient is provided. The method includes placing a first delivery cannula in an operative position inside the mouth of the patient with a distal end of the first delivery cannula disposed adjacent to the patient's laryngeal inlet, releasably securing the first delivery cannula in the operative position, and delivering a flow of the gas to the patient through the distal end of the first delivery cannula with the first delivery cannula secured in the operative position.

In some arrangements, an oral gas catheter and/or method of inducing a gas in a patient as disclosed herein is preferably capable of providing one or more of increased efficiency in anesthesia monitoring, reduce oxygen consumption by up to 40% per medical procedure surgery, accelerate turn-around times for MAC procedures by up to 30-40%, and/or make possible faster rescue of patients following complications such as hypoxia. The oral gas catheter may be capable in some configurations and uses of facilitating more efficient oxygenation in hypoxic situations, reduce hospital oxygen utilization, minimize tissue injury in the patient's nasal passages, reduce the equipment needed for oxygen monitoring, reduce catheter invasive complexity, and/or reduce or eliminate the need to sedate a patient during catheter administration. In many situations, the oral gas catheter can be used for elective anesthesia situations. These and other aspects, arrangements, features, and/or technical effects will become apparent upon detailed inspection of the figures and the following description.

DETAILED DESCRIPTION OF THE INVENTION

The intended purpose of the following detailed description of the invention and the phraseology and terminology employed therein is to describe what is shown in the drawings, which include the depiction of and/or relate to one or more nonlimiting embodiments of the invention, and to describe certain but not all aspects of what is depicted in the drawings, including the embodiment(s) to which the drawings relate. The following detailed description also identifies certain but not all alternatives of the embodiment(s) depicted in the drawings. As nonlimiting examples, the invention encompasses additional or alternative embodiments in which one or more features or aspects shown and/or described as part of a particular embodiment could be eliminated, and also encompasses additional or alternative embodiments that combine two or more features or aspects shown and/or described as part of different embodiments. Therefore, the appended claims, and not the detailed description, are intended to particularly point out subject matter regarded to be aspects of the invention, including certain but not necessarily all of the aspects and alternatives described in the detailed description.

To facilitate the description provided below of the embodiment(s) represented in the drawings, relative terms, including but not limited to, "proximal," "distal," "anterior," "posterior," "vertical," "horizontal," "lateral," "front," "rear," "side," "forward," "rearward," "top," "bottom," "upper," "lower," "above," "below," "right," "left," etc., may be used in reference to the orientation of the oral oxygen catheter as represented in the drawings and/or during its use. All such relative terms are useful to describe the illustrated embodiment(s) but should not be otherwise interpreted as limiting the scope of the invention. While the description and drawings may disclose certain dimensions, such dimensions are for example purposes only and are not otherwise intended as limitations.

Figures 3A, 3B:
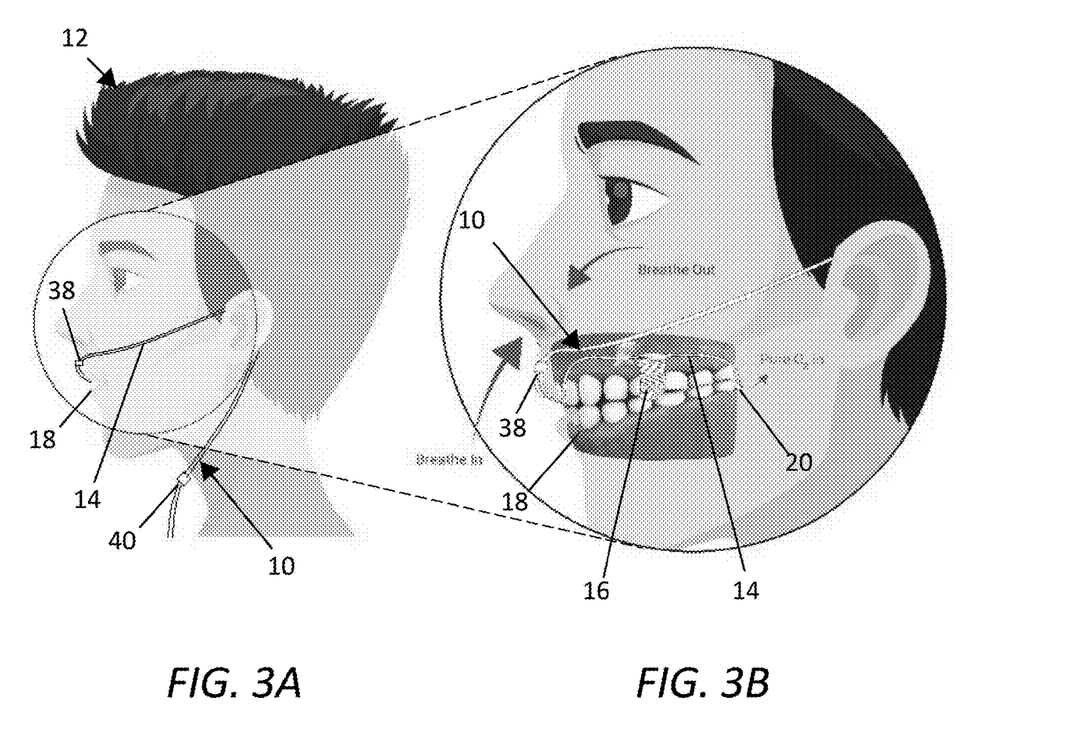
FIG. 3A illustrates a side view of an oral oxygen catheter according to some aspects of the present invention disposed in an operative position on a patient.
FIG. 3B is an enlarged side view of the oral oxygen catheter and patient of FIG. 3A with portions cutaway to be able to see the positioning of the catheter inside the mouth of the patient.

Turning now to the nonlimiting embodiments represented in the drawings, FIGS. 3A and 3B depict an oral gas catheter 10 (sometimes referred to herein as simply "catheter" as a matter of convenience) according to aspects of the invention arranged in an operative position for orally administering and inducing oxygen and/or other gasses into the lungs of a patient 12. The oral gas catheter 10 may be used as an oxygen catheter to deliver pure oxygen to a patient, for example during a MAC-assisted operative procedure or in other circumstances where delivering pure oxygen to a patient is needed, for example, to counteract a hypoxic state of the patient. However, the catheter 10 is not limited to use only with pure oxygen, but may be used to deliver other types of gases orally to a patient in other types of medical procedures and/or for other types of medical needs. Thus, while the catheter 10 may in some instances be described as an oxygen catheter, it is understood that the catheter 10 is not limited to use with only oxygen, but may be used to orally induce other gases under pressure into the lungs of a patient.

Figure 4:
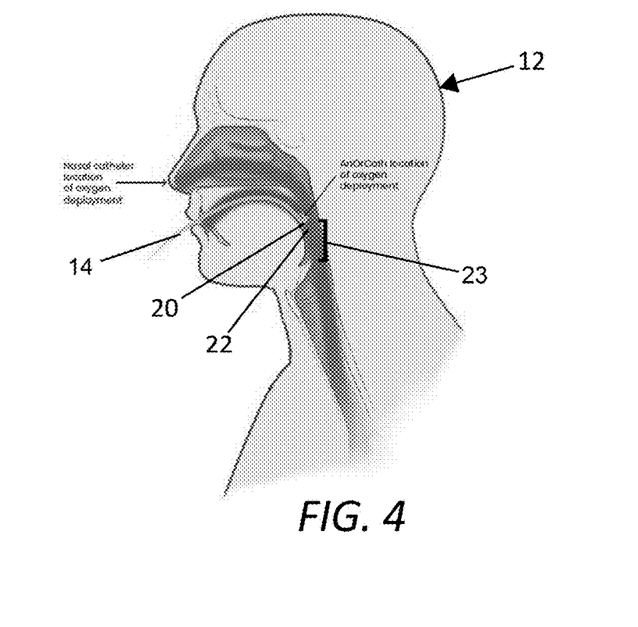
FIG. 4 illustrates the air flow path of oxygen from the oral oxygen catheter in the operative position of FIGS. 3A and 3B from adjacent the laryngeal inlet to the trachea.

The catheter 10 includes at least one delivery cannula 14 that is configured to be inserted into the mouth 18 of the patient 12, such that in the operative position a distal end 20 of the delivery cannula 14 is disposed adjacent the patient's laryngeal inlet 22 (FIG. 4), preferably so that a gas passing through the cannula 14 and existing its distal end 20 is discharged directly into an anatomical dead space 23 of the patient's airway (corresponding to the upper anatomical dead space of the patient's airway represented in FIG. 2). A clip 16 coupled to the delivery cannula 14 is configured to releasably clip to one or more of the patient's teeth, preferably along the side of the patient's mouth 18, to secure the delivery cannula 14 in the operative position with its distal end 20 disposed at or immediately adjacent the laryngeal inlet 22. Preferably, the distal end 20 is disposed between the rear-most tooth of the patient 12 and the laryngeal inlet 22. Thus, in the operative position, the catheter 10 is positioned to deliver a flow of gas, such as oxygen, orally to a patient from the distal end 20 of the cannula 14 directly into the laryngeal inlet 22 of the patient and preferably directly into an anatomical dead space 23 of the patient's airway. As best seen in FIG. 4, this oral placement of the catheter 10 significantly reduces the length that oxygen emitted from the catheter 10 must travel to reach the patient's lungs in relation to the length required from a nasal oxygen catheter. Moreover, in FIG. 4 it can be appreciated that by locating the distal end 20 of the cannula 14 at the entry to the anatomical dead space 23 of the patient's airway, the cannula 10 addresses the inability of prior art nasal oxygen catheters to fully charge the anatomical dead space 23 with oxygen. Placing the distal end 20 of the cannula 14 near or within the anatomical dead space 23 enables the dead space 23 to be filled with pure oxygen instead of simply containing air (containing about 21% oxygen). This benefit exists for MAC sedation procedures and continues during such a procedure and during post-operative monitoring phases. Therefore, in the operative configuration represented in FIGS. 3B and 4, the catheter 10 addresses and overcomes or reduces many of the challenges described hereinbefore with nasal oxygen catheters.

Figures 5, 6:
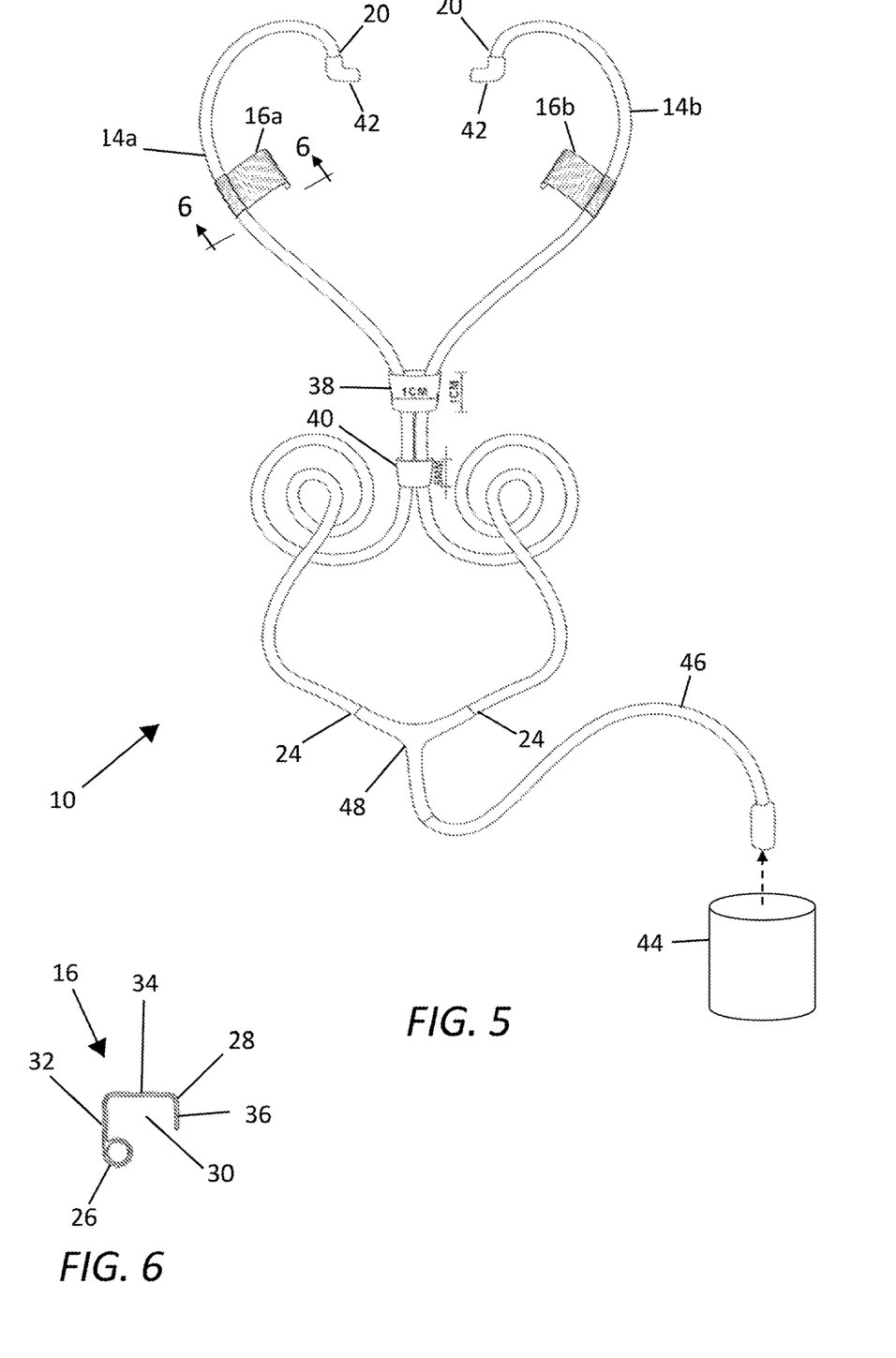
FIG. 5 shows the oral oxygen catheter of FIG. 3A in a first use configuration.
FIG. 6 is an end view of a clip on the oral oxygen catheter generally along the lines 6-6 of FIG. 5.

As best seen in FIG. 5, in one example embodiment, the oral gas catheter 10 includes two delivery cannulas 14, referred to herein as first and second delivery cannulas 14a and 14b (for convenience, the delivery cannulas 14a and 14b may hereinafter be collectively referred to as cannulas 14). Each delivery cannula 14a and 14b extends between its distal end 20 and a proximal end 24. As best seen in FIG. 3A, each delivery cannula 14a and 14b has a length sufficiently long such that they can extend from approximately the patient's laryngeal inlet, out the front of the mouth, back up and around the patient's ear, and downwardly to at least in front of the patient's neck, and preferably further down to the upper chest of the patient. Typically, the lengths of the cannulas 14 may range from about 120 cm to about 300 cm between a coupler 38 and a T-coupling 48 shown in FIG. 5. In some arrangements, the length of each delivery cannula 14 between the coupler 38 and its respective distal end 20 is about 15 cm to about 90 cm, and more preferably about 30 cm to about 60 cm. The delivery cannulas 14 are preferably made of a soft, flexible, biocompatible material, such as a thermoplastic or similar material. In the present example, both delivery cannulas 14 are tubular, medical grade, soft PVC materials, and the connectivity plugs to any types of oxygen source is the same.

Two clips 16, sometimes referred to as first and second clips 16a and 16b, are provided for releasably securing each of the first and second delivery cannulas 14a and 14b to the patient's teeth on opposite sides of mouth. The first clip 16a is disposed on the first delivery cannula 14a, and the second clip 16b is disposed on the second delivery cannula 14b. Each clip 16 is slidably mounted to its respective delivery cannula 14 such that the clip 16 can slide axially along the length of the cannula 14. As best seen in FIG. 6, each clip 16 includes a collar 26 defining an opening sized to receive the delivery cannula 14. Preferably the opening in the collar 26 is sized so that the cannula 14 can slide axially through the collar 26. In this example, the collar 26 has a cylindrical shape that is substantially complementary to the outer diameter of its respective delivery cannula 14. A hook 28 extends from the collar 26 and defines a trough 30 that is configured to receive one or more of the patient's side teeth therein so as to releasably clip to a tooth (or teeth). The hook 28 includes a first portion 32 that extends tangentially away from the collar 26, a second portion 34 that extends orthogonally from a distal end of the first portion 32, and a third portion 36 that extends orthogonally from a distal end of the second portion 34 back generally in the direction toward the collar 26. Due to the tangential connection, the collar 26 extends laterally from the first portion 32 over the trough 30. In this example, each of the first portion 32 and the second portion 34 has a length of approximately 1.5 cm in order to be able to receive a side tooth of a typical adult human within the trough 30. In this configuration, the first portion 32, second portion 34, and third portion 36, define a generally rectangular U-shaped trough 30. However, the collar 26 and the hook 28 may have other shapes and/or configurations. The clips 16 are preferably made of a rigid or resilient biocompatible polymer material, although other materials may be used.

In addition to the coupler 38 and T-coupling 48 mentioned above in reference to FIG. 5, the cannulas 14 may be connected or otherwise held together by additional means. In FIG. 5, the first and second delivery cannulas 14a and 14b are shown as further held together by a second coupler 40, such that the cannulas 14 are secured together with at least two couplers, referred to herein as first and second couplers 38 and 40. The first coupler 38 is disposed axially along the delivery cannulas 14 between the second coupler 40 and the distal ends 20 of the delivery cannulas 14. The first coupler 38 is also disposed axially along the delivery cannulas 14 between each of the first and second clips 16a and 16b and the second coupler 40. The second coupler 40 is spaced axially from the proximal ends 24 of the delivery cannulas 14. In this way, the distal ends 20 of the delivery cannulas 14 are free ends, that is, free to move about independently in an unrestricted manner relative to each other. One or both of the first and second couplers 38 and 40 may be slide couplers configured to slide axially along the delivery cannulas 14 so that the lengths of the free distal and proximal ends 20 and 24 of the delivery cannulas 14 can be adjusted to fit the size and shape of different patients. It is foreseeable that the couplers 38 and 40 could be adjusted along the length of the delivery cannulas 14 to be located directly at the ends of the cannulas 14. In this example, each coupler 38 and 40 includes a body portion with a pair of bores extending generally parallel to each other therethrough which slidably receive the delivery cannulas 14 therein. However, other configurations for the couplers 38 and 40 are also possible.

A discharge nozzle 42 is disposed on the distal end 20 of at least one of, and preferably each of the first and second delivery cannulas 14a and 14b. The discharge nozzle 42 has a hook shape configured to hook the distal end 20 of each delivery cannula 14 behind the furthest back tooth of the patient 12 and thereby further secure the delivery cannulas 14 in their operative positions with each of their discharge nozzles 42 located adjacent the laryngeal inlet 22 so as to be preferably capable of discharging a gas directly into the anatomical dead space 23, for example, as represented in FIG. 4. In this example, each discharge nozzle 42 has the shape of a 90° elbow. However, the discharge nozzle 42 may have different shapes, and in some arrangements may be omitted entirely.

Figure 7:
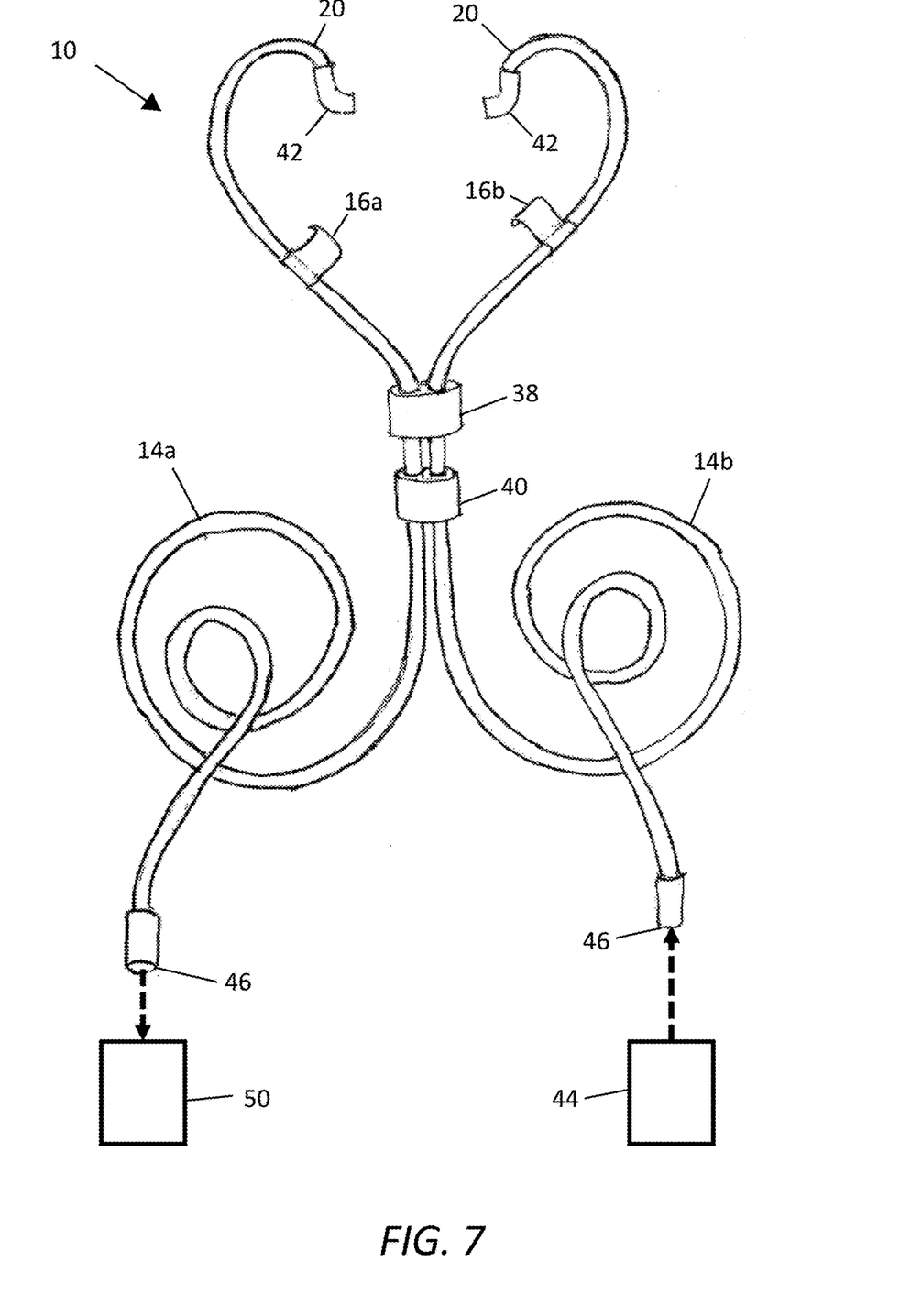
FIG. 7 shows the oral oxygen catheter of FIG. 3A in a second use configuration.

As seen in FIGS. 5 and 7, the oral gas catheter 10 may be configured in at least two different ways to accommodate different use needs. In the configuration of FIG. 5, the catheter 10 is used solely for supplying a flow of gas, such as oxygen, to the discharge nozzles 42 disposed on the distal ends 20 of the first and second delivery cannulas 14a and 14b, for example, for inducing oxygen into the patient's lungs. In this configuration, each of the first and second delivery cannulas 14a and 14b receives a supply of pressurized gas from a gas supply 44. To accomplish this, the proximal end 24 of each of the first and second delivery cannulas 14a and 14b is shown as coupled to the gas supply 44 via the T-coupling 48 and a gas supply tube 46. The proximal end 24 of the first delivery cannula 14a is coupled to a first branch of the T-coupling 48, the proximal end 24 of the second delivery cannula 14b is coupled to a second branch of the T-coupling 48, and a distal end of the gas supply tube 46 is coupled to a third branch of the T-coupling 48. The proximal end of the gas supply tube 46 is operatively coupled to the gas supply 44 so as to deliver pressurized gas to the delivery cannulas 14. The proximal ends 24 of the delivery cannulas 14a and 14b may be removable from the T-coupling 48, for example, by sliding their proximal ends 24 out of their respective branches of the T-coupling 48 for quickly changing into the configuration shown in FIG. 7.

Figure 10:
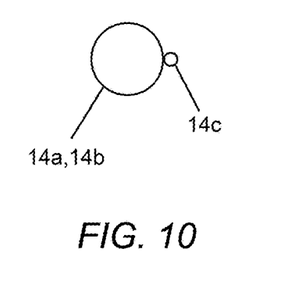
FIG. 10 schematically represents a cross-sectional view of a cannular of any of the oral oxygen catheters of FIGS. 3A, 3B, 5, and 7, and shows a fine catheter or cannula incorporated onto the cannula to provide for continuous carbon dioxide sampling simultaneously with the delivery of oxygen through both cannulas of the oral oxygen catheter.

In FIG. 7, the oral gas catheter 10 is configured to be used to both deliver oxygen or other gas for inducing the gas into a patient's lungs, and also sense the presence of a second gas, such as carbon dioxide, without having to introduce a whole other catheter into the patient's mouth. In this configuration, rather than being coupled to the same gas supply tube as in the configuration of FIG. 5, the proximal end 24 of each of the first and second delivery cannulas 14a and 14b is operatively connected with a different mechanism. In this example, the proximal end 24 of the second delivery cannula 14b is operatively coupled to the gas supply 44 (for example, pure oxygen), and the proximal end 24 of the first delivery cannula 14a is operatively coupled to a gas sensor 50, such as a carbon dioxide sensor. Alternatively, as schematically represented in FIG. 10, an additional fine catheter or cannula 14c can be incorporated onto either or both cannulas 14a and 14b to provide for carbon dioxide sampling and provide the capability for continuous monitoring of carbon dioxide simultaneously with the delivery of oxygen through both cannulas 14a and 14b. The gas sensor 50 may be configured to draw gases through the first delivery cannula 14a from its distal end 20, whereas the gas supply 44 may be configured to push gases through the second delivery cannula 14b out of the discharge nozzle 42 disposed on its distal end 20. In this way, the catheter 10 can simultaneously and/or alternatingly both deliver a stream of oxygen or other gas to a patient's mouth and monitor the presence of a second gas, such as carbon dioxide, by drawing gas from the patient's mouth to the sensor 50. The catheter 10 can also be quickly and easily changed between the configuration of FIG. 5 and the configuration of FIG. 7.

Figure 8:
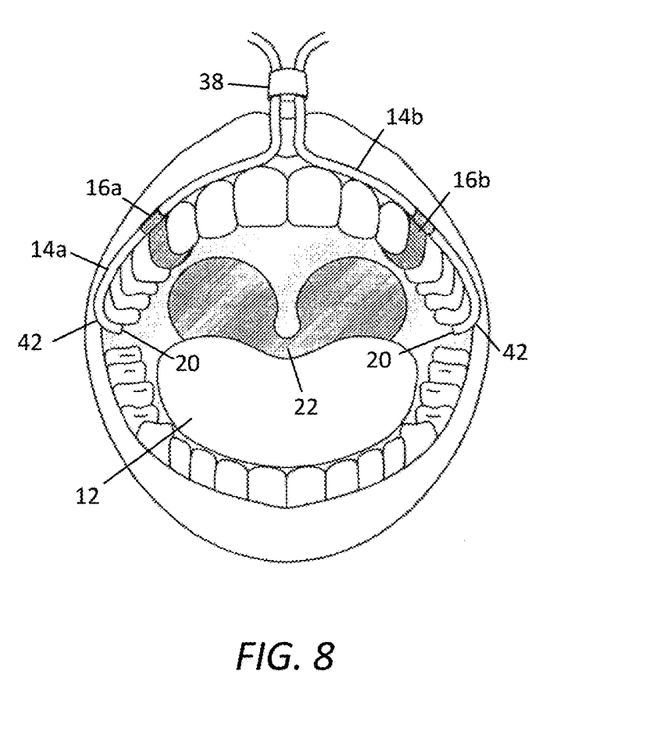
FIG. 8 is a view looking into the open mouth of a patient with the oral oxygen catheter of the present invention in an operative position.
Figure 9:
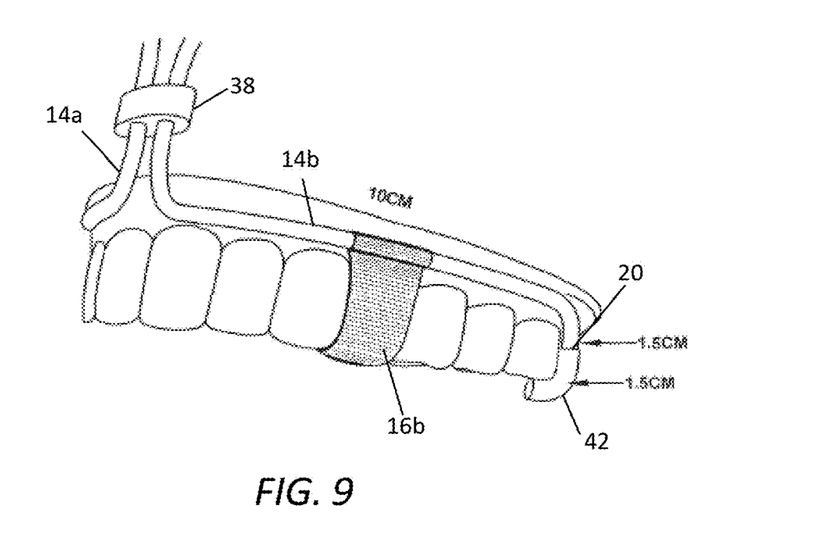
FIG. 9 is an isometric view of the oral oxygen catheter in the operative position of FIG. 8 with only portions of the catheter, teeth, and gum shown for clarity.

As best seen in FIGS. 3A, 3B, 8, and 9, the oral gas catheter 10 provides for a method of inducing oxygen or other gas to the patient's lungs through the mouth 18 rather than through the nose. One example process for using the catheter 10 includes first placing at least one of the delivery cannulas 14 in an operative position inside the patient's mouth 18 with the discharge nozzle 42 at its distal end 20 disposed at the back of the mouth adjacent to the patient's laryngeal inlet 22. The delivery cannula 14 is then releasably secured in the operative position, for example, by securing its clip 16 to one or more of the patient's teeth on one side of mouth. As best seen in FIGS. 8 and 9, the discharge nozzle 42 at the distal end 20 of the delivery cannula 14 is preferably disposed immediately behind the back of the patient's rear-most tooth. The discharge nozzle 42 may be hooked around the back of the back tooth to further stabilize the delivery cannula 14 in its operative position. With the delivery cannula 14 secured in its operative position in the patient's mouth, a flow of oxygen or other gas can then be delivered to the patient through the discharge nozzle 42 so as to deliver the flow of gas directly to the back part of the patient's mouth adjacent to the laryngeal inlet 22 and preferably into the anatomical dead space 23. In the present example, each of the first delivery cannula 14a and the second delivery cannula 14b is secured in the operative position inside the patient's mouth, with one delivery cannula disposed along the laterally exterior side of the gum on each of the left and right sides of the patient's upper jaw, and with the first clip 16a releasably secured to one or more teeth on one side of the jaw, and the second clip 16b releasably secured to one or more teeth on the other of the jaw. The discharge nozzle 42 on each delivery cannula 14a and 14b is hooked around the back tooth and points toward the laryngeal inlet 22 such that the flows of gas exiting the nozzles are directed toward the laryngeal inlet 22 and into the anatomical dead space 23. In this operative position, it is also possible to connect one of the delivery cannulas 14 to the gas supply 44 and the other of the delivery cannulas to the gas sensor 50 to both deliver a flow of gas to the patient and sense the presence of carbon dioxide or other gas without having to modify the placement of the delivery cannulas or introduce a second catheter into the patient's mouth.

To further help the catheter 10 remain in the operative position during use, the couplers 38 and 40 be adjusted such that the delivery cannulas 14 can be draped over the left and right ears of the patient as shown in FIG. 3A. For example, the first slide coupler 38 may be adjusted along the length of the delivery cannulas 14 to be located exterior of the mouth directly below the nose, as best seen in FIGS. 3A, 3B, and 9. Alternatively, the cannulas 14 may be opposed to the front of the upper incisor teeth by the first coupler 38 under the upper lip of the patient. The second slide coupler 40 may be adjusted along the length of the delivery cannulas 14 toward the proximal ends 24 so that the first delivery cannula 14a can be wrapped back over the right ear of the patient, the second delivery cannula 14b can be wrapped back over the left ear of the patient, and the delivery cannulas 14 rejoined below the chin of the patient at the location of the second slide coupler 40. Thus, the catheter 10 also can be easily adjusted to fit on different sized patients and remains secured in its operative position with a relatively comfortable engagement to the patient.

Both delivery cannulas 14 in some arrangements perform similar to varying oxygen flow rates controlled by pressure regulators, which typically deliver oxygen at pressures of about 5 to 8 psi (about 355 to 550 millibar). The standardizations applicable for conventional catheters, for example for material composition, functionality, patient comfort and packaging may be in accordance with FDA and HIPAA regulations guidelines.

It is believed that the oral gas catheter 10 may provide one or more advantages relative to nasal oxygen catheters because it is placed intra-orally closer to the laryngeal inlet and closer to the lungs. For example, in some arrangements, blood oxygen levels may be increased in shorter time without the need for high oxygen inflow. Little or no oxygen is wasted into atmosphere, which may save oxygen utility by 25-40% on an average clinical procedure. It may be possible to attain 80% oxygen saturation within 1-2 minutes of inflow, which may result in 50% times savings as compared to nasal catheters. The catheter 10 may allow anatomical dead space to be completely charged with oxygen due to the catheter's placement near laryngeal inlet. The intra-oral placement may in some cases augment pharyngeal pressure because the patient's mouth could remain closed and the nostrils could be blocked, which may allow for faster oxygen saturation. Due to its placement in the mouth, high flow oxygen application may not be required, and nasal inflammation from the application of gas through the nose is eliminated. Intraoral oral pressure buildup and gastric dilatations can be averted when the mouth is opened, while still ensuring that oxygen is supplied through the oral pathway. The need for any type of airway modifications may be unnecessary since the nasal airways are completely bypassed. Dryness may be reduced or eliminated along the oxygenation pathway due to natural salivation in the oral cavity, regardless of whether there is a low oxygen flow rate or a high oxygen flow rate. Due to its bilateral tube design, the catheter 10 makes it feasible to implement a quick or emergency switch over to carbon dioxide monitoring in dire hypoxic situation at any given time. One of the bilateral tubes (delivery cannulas 14) can be temporarily utilized for $CO_2$ monitoring. For example, when $CO_2$ data is needed, the $CO_2$ device may cease oxygen flow and trigger $CO_2$ suction for anesthetist's analysis. The favorable position of the distal ends 20 of the catheter 10 at the intraoral position (closest to lungs entry point) may in some situations quickly salvage a hypoxic state in a patient as indicated in MAC due to varying anesthetic depths. For example, because anesthetic depth and oxygenation failure are directly proportional, a continuous increase in anesthetic depth can be rapidly countered by first increasing oxygen flow momentarily to increase the oxygen level in the lungs. If a respiratory arrest is emergent, a quick switch to ambulatory manual ventilation can be restored to overcome acute hypoxia and prevent cardiac arrest. The catheter 10 may enable faster procedural turn-around times owing to minimized complications arising due to oxygen management. Because the oral gas catheter 10 may make it possible to provide oxygenation without the need to interrupt or delay operative procedures, the catheter 10 may enable the implementation of one or more counter measures that could save lives and be important in MAC-assisted procedures.

As previously noted above, though the foregoing detailed description describes certain aspects of one or more particular embodiments of the invention, alternatives could be adopted by one skilled in the art. For example, the oral gas catheter 10 and its components could differ in appearance and construction from the embodiments described herein and shown in the drawings, functions of certain components of the oral gas catheter 10 could be performed by components of different construction but capable of a similar (though not necessarily equivalent) function, and various materials could be used in the fabrication of the oral gas catheter 10 and/or their components. As such, and again as was previously noted, it should be understood that the invention is not necessarily limited to any particular embodiment described herein or illustrated in the drawings.

The invention claimed is:

1. An oral gas catheter placed in the mouth of a patient to administer oxygen under pressure into the lungs of the patient during a monitored anesthesia care-assisted operative procedure, the oral gas catheter comprising:
   a delivery cannula secured inside the patient's mouth, the delivery cannula being disposed along a laterally exterior side of the gum on one side of the patient's upper jaw and having a distal end disposed adjacent the patient's laryngeal inlet;
   a discharge nozzle disposed at the distal end of the delivery cannula, the discharge nozzle being hooked behind a back tooth of the upper teeth on the one side of the patient's upper jaw and pointing toward the laryngeal inlet such that oxygen exiting the distal end is directed toward the laryngeal inlet and into an anatomical dead space of the airway of the patient, wherein the delivery cannula defines an elbow between the laterally exterior side of the gum and the back tooth so that the delivery cannula extends downward from the laterally exterior side of the gum and behind the back tooth; and
   a clip disposed on the delivery cannula and securing the delivery cannular to at least one tooth of the upper teeth on the one side of the patient's upper jaw.

2. The oral gas catheter of claim 1, wherein the clip is slidably disposed on the delivery cannula such that the clip can slide axially along the delivery cannula.

3. The oral gas catheter of claim 2, wherein the clip comprises a collar slidingly mounted around the delivery cannula and a hook extending from the collar, wherein the hook defines a trough that receives and releasably mounts to the tooth.

4. The oral gas catheter of claim 3, wherein the hook includes a first portion extending away from the collar, a second portion extending orthogonally from a distal end of the first portion, and a third portion extending orthogonally from a distal end of the second portion, wherein the first, second, and third portions define the rectangular trough.

5. The oral gas catheter of claim 4, wherein the first portion extends tangentially from the collar.

6. The oral gas catheter of claim 1, wherein the discharge nozzle defines a second elbow behind the back tooth so that the discharge nozzle extends medially inward behind the back tooth and toward the laryngeal inlet.

7. An oral gas catheter placed in the mouth of a patient to administer oxygen under pressure into the lungs of the patient during a monitored anesthesia care-assisted operative procedure, the oral gas catheter comprising:
  a first delivery cannula secured inside the patient's mouth, the first delivery cannula being disposed along a first laterally exterior side of the gum on a first side of the patient's upper jaw and having a distal end disposed adjacent the patient's laryngeal inlet;
  a first discharge nozzle disposed at the distal end of the first delivery cannula, the first discharge nozzle being hooked behind a back tooth of the upper teeth on the first side of the patient's upper jaw and pointing toward the laryngeal inlet such that oxygen exiting the distal end of the first delivery cannula is directed toward the laryngeal inlet and into an anatomical dead space of the airway of the patient, wherein the first delivery cannula defines an elbow between the first laterally exterior side of the gum and the back tooth of the upper teeth on the first side of the patient's upper jaw so that the first delivery cannula extends downward from the first laterally exterior side of the gum and behind the back tooth of the upper teeth on the first side of the patient's upper jaw;
  a second delivery cannula secured inside the patient's mouth, the second delivery cannula being disposed along a second laterally exterior side of the gum on a second side of the patient's upper jaw and having a distal end disposed adjacent the patient's laryngeal inlet;
  a second discharge nozzle disposed at the distal end of the second delivery cannula, the second discharge nozzle being hooked behind a back tooth of the upper teeth on the second side of the patient's upper jaw and pointing toward the laryngeal inlet such that oxygen exiting the distal end of the second delivery cannula is directed toward the laryngeal inlet and into the anatomical dead space of the airway of the patient;
  a first clip disposed on the first delivery cannula, the first clip securing the first delivery cannula to at least a first tooth of the upper teeth on the first side of the patient's upper jaw;
  a second clip disposed on the second delivery cannula, the second clip securing the second delivery cannula to at least a second tooth of the upper teeth on the second side of the patient's upper jaw opposite the first side of the patient's upper jaw; and
  a first coupler coupling the first delivery cannula to the second delivery cannula, wherein the first and second clips are disposed between the first coupler and the respective distal ends of the first and second delivery cannulas.

8. The oral gas catheter of claim 7, further comprising:
  a second coupler coupling the first delivery cannula to the second delivery cannula, wherein first coupler is disposed axially along the first and second cannulas between the second coupler and the first and second clips.

9. The oral gas catheter of claim 8, wherein at least one of the first coupler and the second coupler comprises a slide coupler that is slidably mounted to the first and second delivery cannulas and configured to be able to slide axially along the first and second delivery cannulas.

10. The oral gas catheter of claim 7, wherein at least one of the first clip and the second clip comprises a collar slidingly mounted around the respective first or second delivery cannula and a hook extending from the collar, wherein the hook defines a trough that receives and releasably mounts to the respective first tooth or second tooth.

11. The oral gas catheter of claim 7, further comprising:
  a gas supply tube supplying the oxygen to each of the first cannula and the second cannula; and
  a T-coupling that operatively couples each of the first cannula and the second cannula to the gas supply tube.

12. The oral gas catheter of claim 7, in combination with a pressurized oxygen supply and a carbon dioxide sensor,
  wherein the pressurized oxygen supply is coupled to a proximal end of the first cannula to deliver the oxygen to the distal end of the first cannula; and
  wherein the carbon dioxide sensor is coupled to a proximal end of the second cannula for sensing carbon dioxide at the distal end of the second cannula.

13. The oral gas catheter of claim 7, wherein:
  the first discharge nozzle defines a second elbow behind the back tooth of the upper teeth on the first side of the patient's upper jaw so that the first discharge nozzle extends medially inward behind the back tooth of the upper teeth on the first side of the patient's upper jaw and toward the laryngeal inlet.

14. A method of inducing oxygen into an airway of a patient during a monitored anesthesia care-assisted operative procedure, the method comprising:
  placing a first delivery cannula inside the mouth of the patient;
  releasably securing the first delivery cannula inside the patient's mouth so that the first delivery cannula is disposed along a first laterally exterior side of the gum on a first side of the patient's upper jaw;
  hooking a first discharge nozzle at a distal end of the first delivery cannula behind a back tooth of the upper teeth on the first side of the patient's upper jaw and pointing the distal end toward the laryngeal inlet such that oxygen exiting the distal end is directed toward the laryngeal inlet and into an anatomical dead space of the airway of the patient wherein the first delivery cannula defines an elbow between the first laterally exterior side of the gum and the back tooth and the hooking of the first discharge nozzle behind the back tooth comprises extending the first delivery cannula downward from the first laterally exterior side of the gum and behind the back tooth; and
  delivering a flow of the oxygen to the patient through the distal end of the first delivery cannula so that the oxygen is discharged into the anatomical dead space of the airway.

15. The method of claim 14, wherein the step of releasably securing comprises securing a first clip disposed on the first delivery cannula to at least a first tooth of the upper teeth on the one side of the patient's upper jaw.

16. The method of claim 14, further comprising:
  placing a second delivery cannula in an operative position inside the mouth of the patient with a distal end of the second delivery cannula disposed adjacent to the patient's laryngeal inlet, wherein the second delivery cannula is coupled to the first delivery cannula;
  releasably securing the second delivery cannula in the operative position; and
  sensing the presence of a second gas at the distal end of the second delivery cannula with a sensor.

17. The method of claim 16, wherein the second gas is carbon dioxide.

18. The method of claim 14, wherein the first discharge nozzle defines a second elbow behind the back tooth and the hooking of the first discharge nozzle behind the back tooth further comprises extending the first discharge nozzle medially inward behind the back tooth and toward the laryngeal inlet.

\* \* \* \* \*